US00PP32145P2

(12) United States Plant Patent
Van Swieten

(10) Patent No.: US PP32,145 P2
(45) Date of Patent: Sep. 1, 2020

(54) ***PHALAENOPSIS* ORCHID PLANT NAMED 'PHALGUAJO'**

(50) Latin Name: ***Phalaenopsis* hybrid**
Varietal Denomination: PHALGUAJO

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/602,851

(22) Filed: Dec. 11, 2019

(51) Int. Cl.
*A01H 6/62* (2018.01)
*A01H 5/02* (2018.01)

(52) U.S. Cl.
USPC ..... Plt./311

(58) Field of Classification Search
USPC ..... Plt./311
CPC ..... A01H 6/62; A01H 5/02
See application file for complete search history.

*Primary Examiner* — Annette H Para
(74) *Attorney, Agent, or Firm* — Jondle & Associates, P.C.

(57) ABSTRACT

A new and distinct variety of *Phalaenopsis* plant named 'PHALGUAJO', particularly characterized by having copper flowers with red-yellow and white, dotted lips, panicle inflorescence, bump and ridge on the lip, and is propagated by meristem tissue culture, is disclosed.

3 Drawing Sheets

Genus and species: *Phalaenopsis* hybrid.
Variety denomination: 'PHALGUAJO'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGUAJO'.

The new *Phalaenopsis* plant is a product of a planned breeding program conducted by the inventor in Bleiswijk, the Netherlands. The objective of this breeding program was to create a new *Phalaenopsis* plant with panicle inflorescences and attractive copper flowers with red-yellow and white, dotted lips, suitable for potted plant production.

The new *Phalaenopsis* plant 'PHALGUAJO' is a result of cross-pollination made by the inventor in May 2010 in Bleiswijk, the Netherlands, of the proprietary female, or seed parent, *Phalaenopsis* hybrid '01-1859' (unpatented) with the proprietary male, or pollen parent, *Phalaenopsis* hybrid '22286-05' (unpatented).

The new *Phalaenopsis* was selected by the inventor as a single plant within the progeny of the stated cross-pollination in a controlled greenhouse in Bleiswijk, the Netherlands, in June 2013. Asexual reproduction of the new *Phalaenopsis* plant by meristem tissue culture since 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Apr. 16, 2019, by Applicant who obtained the subject matter disclosed directly from the inventor. 'PHALGUAJO' has not been made publicly available or sold anywhere in the world prior to the effective filing date of this application with the exception of sales or disclosures made one year or less before the effective filing date of this claimed invention by Applicant who obtained 'PHALGUAJO' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALGUAJO' as a new and distinct variety of *Phalaenopsis* plant:

1) Copper flowers;
2) Red-yellow and white, dotted lips;
3) Panicle inflorescence; and
4) Bump and ridge on the lip.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, the Netherlands, from 50-week-old plants in November 2019. Colors in the photographs may differ from the color values cited in the detailed botanical description, which accurately describe the actual colors of the new variety.

DESCRIPTION OF THE NEW VARIETY

Figure 1:
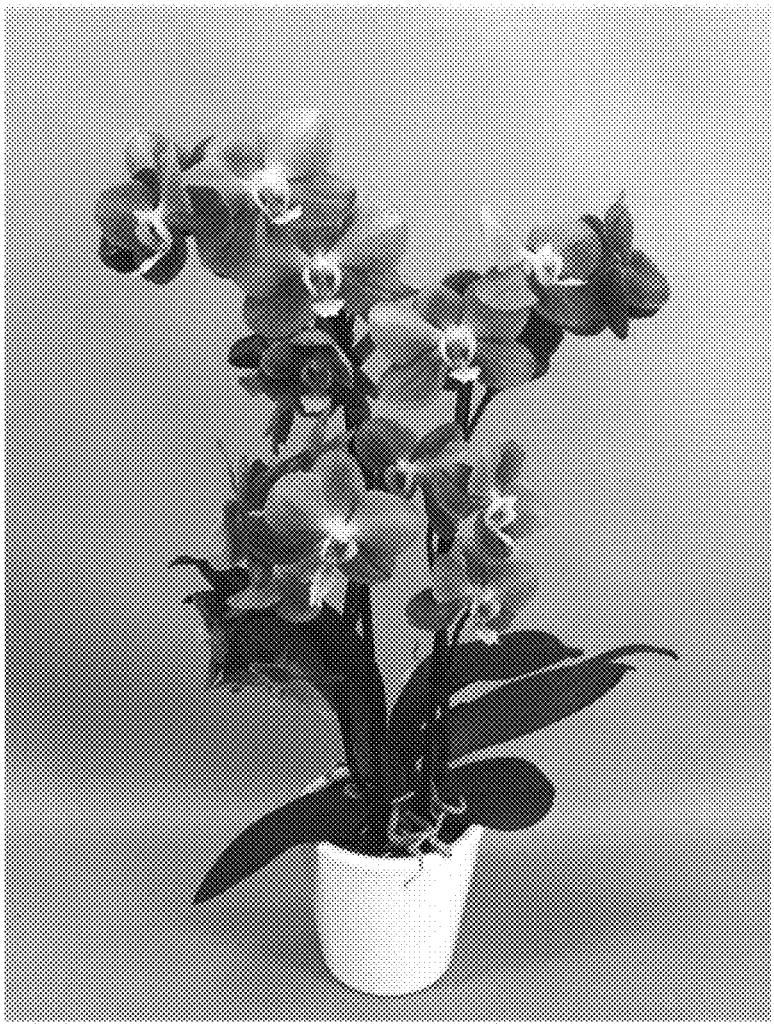
FIG. 1 shows the overall plant habit, including blooms and foliage of 'PHALGUAJO'.
Figure 2:
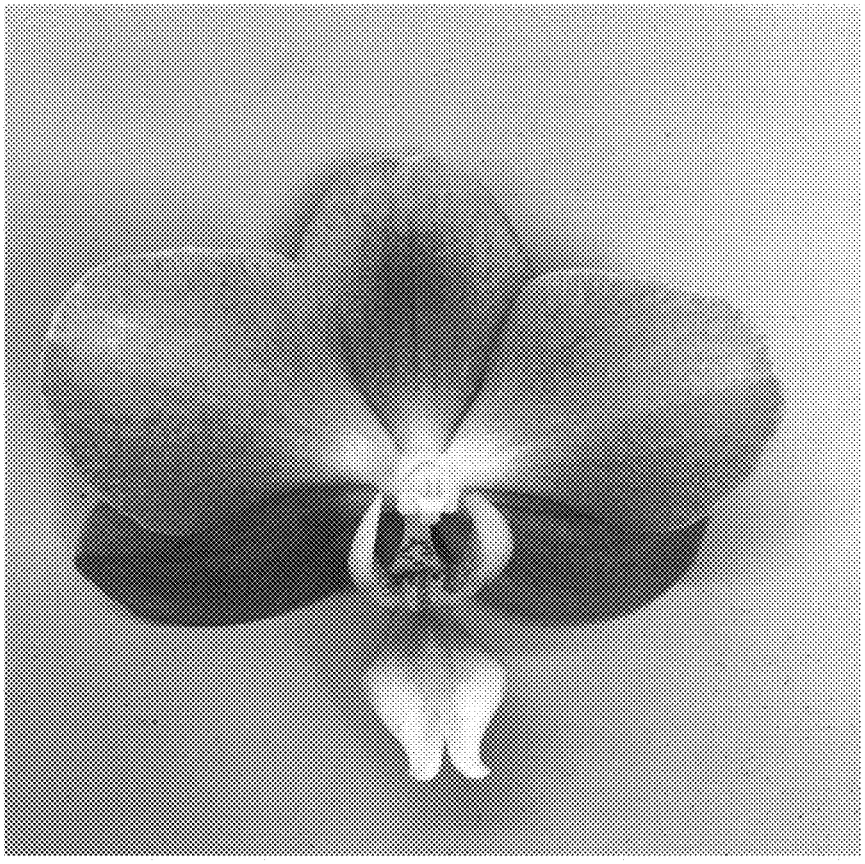
FIG. 2 shows a close-up of a flower of 'PHALGUAJO'.
Figure 3:
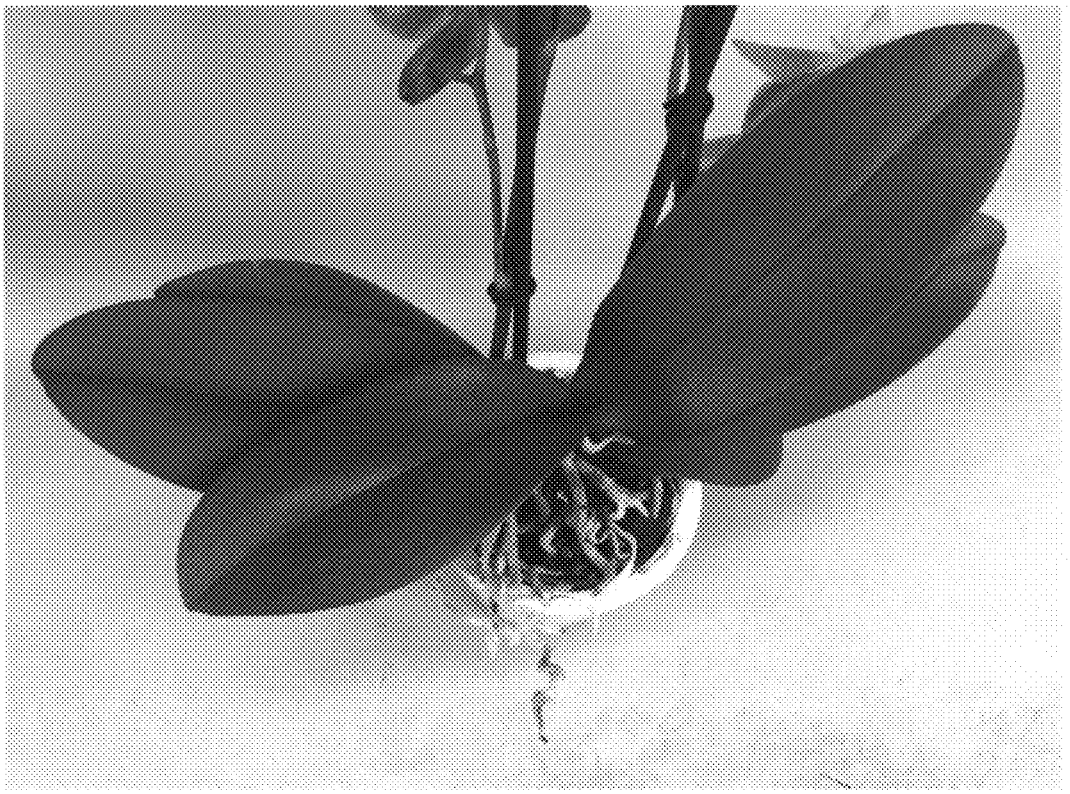
FIG. 3 shows an overhead view of the leaves of 'PHALGUAJO'.

The following detailed description sets forth the distinctive characteristics of 'PHALGUAJO'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in November 2019 on flowering plants which were planted in 9-centimeter (diameter) pots. After in-vitro propagation, the plants were grown in nursery trays for 18-20 weeks, followed by transplantation to 9-centimeter pots and grown in a greenhouse between 27° C. to 29° C. for 25 weeks, continued by a cooling period of 6 weeks between 18° C. to 20° C. and 11 weeks in a greenhouse of 21° C. Flowering occurs after 42 weeks in 9-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALGUAJO'.

Parentage:

*Female parent*.—*Phalaenopsis* cultivar '01-1859' (unpatented).

*Male parent*.—*Phalaenopsis* cultivar '22286-05' (unpatented).

Propagation:

*Type*.—Meristem tissue culture.

Roots:

*Root description*.—Greyed-green (between RHS 190B and 190C) colored roots with branching lateral roots having yellow-green (RHS 144B) colored root tips.

Plant:

*Commercial crop time to flowering*.—Following asexual propagation (in-vitro), the rooted cuttings grow for 18-20 weeks. After transplantation into 9-cm pots, the plants are finished after 40 to 42 weeks.

*Height* (*from soil level to top of inflorescence*).—Approximately 35.0 cm to 40.0 cm.

*Width* (*measured from leaf tips*).—About 28.0 cm to 30.0 cm.

*Vigor*.—Strong.

Leaves:

*Mature leaves*.—Quantity per plant: 6 to 8 leaves are produced before flowering. Length (fully expanded): 17.0 cm to 19.0 cm. Width: 6.5 cm to 7.5 cm. Position of the broadest part of the leaf: In the middle. Shape: Oblong. Base shape: Moderately elongated. Apex: Obtuse unequal. Leaf blade angle with the petiole (measured from the horizontal position): Between 20 degrees and 40 degrees. Leaf margin: Entire. Color: Upper surface: RHS 146A. Lower surface: RHS 146B with a reddish-brown margin (RHS 200B) toward the tip. Texture Upper surface: Smooth. Lower surface: Ribbed, but smooth. Thickness: 1.0 mm to 2.0 mm. Variegation: Absent. Venation: Pattern: Parallel. Color of the midvein: Upper surface: RHS 146A. Lower surface: RHS 146B.

Peduncle:

*Quantity per plant*.—1 to 2.

*Number of flowers per peduncle*.—13 to 18.

*Length*.—35.0 cm to 40.0 cm.

*Diameter*.—5.0 mm to 6.0 mm.

*Strength*.—Strong.

*Aspect*.—Upright to slightly pendant.

*Texture*.—Smooth.

*Color*.—Mix of green (RHS 146C) and reddish-brown (RHS 200B).

*Internode length*.—4.0 cm to 6.0 cm.

Inflorescence description:

*Appearance*.—Upright to slightly pendant, panicle inflorescence with bilaterally symmetrical flowers that open in succession beginning with the lowermost flower.

*Number of inflorescences*.—1 to 2.

*Inflorescence size*.—Height (from base to tip): 270.0 mm to 320.0 mm.

*Flowering time*.—First flowers can be expected 10 to 11 months after planting in a 9-cm pot.

*Flower*.—Height: 65.0 mm to 70.0 mm. Diameter: 75.0 mm to 80.0 mm. Depth of lip: 23.0 mm to 25.0 mm.

*Flower longevity*.—On the plant: 12 to 14 weeks.

*Flower shape*.—Convex.

*Fragrance*.—Absent.

*Flower bud*.—Average size: Medium. Length: 18.0 mm to 20.0 mm. Width: 15.0 mm to 17.0 mm. Shape: Egg shaped. Color: Mix of dark red (RHS 187C) and green (RHS 146D).

*Petals*.—Arrangement: Open/free. Shape: Semi-circular. Apex: Rounded. Margin: Slightly undulated. Length (from base to tip): 36.0 mm to 38.0 mm. Width: 35.0 mm to 37.0 mm. Position of the broadest part of the petal: Toward the base. Color (when fully opened): Upper surface: Basic color: Light yellow (RHS 160D). Over color: Red shade (RHS 182B). Lower surface: Basic color: Light yellow (RHS 160D). Over color: Red (between RHS 182B and 182C). Number of spots and stripes on the petals (upper surface): None. Color of spots and stripes on the petals (upper surface): None. Density of netting of the petals (upper surface): None. Color of the netting (upper. surface): None.

*Dorsal sepal*.—Shape: Elliptic. Apex: Emarginated symmetric. Margin: Entire. Length (from base to tip): 40.0 mm to 42.0 mm. Width: 31.0 mm to 33.0 mm. Position of the broadest part of the dorsal sepals: In the middle. Color (when fully opened): Upper surface: Basic color: Light yellow (RHS 160B). Over color: Red shade (RHS 183C). Lower surface: Basic color: Light yellow (RHS 160D). Over color: Dark pink (RHS 182C) toward the edge. Number of spots and stripes- on the dorsal sepals (upper surface): None. Color of spots and stripes on the dorsal sepals (upper surface): None. Density of netting of the dorsal sepals (upper surface): None. Color of the netting (upper surface): None.

*Lateral sepals*.—Shape: Ovate. Apex: Obtuse asymmetric. Margin: Entire. Length (from base to tip): 38.0 mm to 40.0 mm. Width: 28.0 mm to 31.0 mm. Position of the broadest part of the lateral sepals: At the base. Color (when fully opened): Upper surface: Basic color: Red (RHS 183D). Over color: Hint of greenish-yellow (RHS 151A) at the base and tip.

Lower surface: Basic color: Purplish-red (RHS N77B). Over color: Touch of light yellow-green (RHS 145C) at the base and tip. Number of spots and stripes on the lateral sepals (upper surface): None. Color of spots and stripes on the lateral sepals (upper surface): None. Density of netting of the lateral sepals (upper side): None. Color of the netting (upper side): None.

*Labellum* (*lip*).—Whiskers: Present. Length of whiskers: 2.0 mm to 4.0 mm. Color of whiskers: White (RHS NN155C) with very small dots (RHS N78D). Pubescence on the lip: Absent.

*Lateral lobe*.—Shape: Type III (as described in the International Union for the Protection of New Varieties of Plants (UPOV) Test Guidelines for *Phalaenopsis*); oblong. Margin: Entire. Length: 13.0 mm to 15.0 mm. Width: 5.0 mm to 7.0 mm. Color: Upper surface: Yellow (RHS 9B) at the base and margin on one side (RHS 9A); white (RHS NN155C) toward the other side. Lower surface: Yellowish-pink (RHS N170D) at the base; yellow margin (RHS 9A) on one side and white (RHS NN155C) toward the other side. Number of spots and stripes on the lateral lobe (upper surface): Medium (at the base). Color of spots and stripes on the lateral lobe: RHS 185A. Density of netting of the lateral lobe: None. Color of the netting: None.

*Apical lobe*.—Shape: Rhombic. Margin: Entire. Length: 15.0 mm to 17.0 mm. Width: 13.0 mm to 15.0 mm. Color: Upper surface: Red (RHS 181B to 181C) at the base; yellow (RHS 9C) and white (RHS NN155C) toward the whiskers. Lower surface: Dark yellowish-pink (RHS 181D) at the base; yellow margins (RHS 9C) toward the middle and white (RHS NN155C) dotted (RHS N78C) toward the whiskers. Number of spots and stripes on the apical lobe: Very many small dots. Color of spots and stripes on the apical lobe: RHS N78C. Density of netting of the apical lobe: None. Color of the netting: None. Bump and ridge: Medium.

*Callus*.—Average size: Small. Height: 3.0 mm to 4.0 mm. Length: 3.0 mm to 4.0 mm. Width: 2.0 mm to 3.0 mm. Color: Yellow (RHS 9A) with red spots (RHS 178A). The tip of the callus is serrated.

Reproductive organs:

*Column*.—Length: 8.0 mm to 10.0 mm. Diameter: 4.0 mm to 5.0 mm. Color: White (RHS NN155C) with small purplish-pink dotted region (RHS N78C) toward the tip.

*Pollinia*.—Quantity: 2. Diameter: 0.6 mm to 0.8 mm. Color: Orange-yellow (RHS 23A).

*Ovary*.—Length: 10.0 mm to 12.0 mm. Diameter: 2.0 mm to 3.0 mm.

*Pedicel*.—Length: 31.0 mm to 33.0 mm. Diameter: 2.0 mm to 3.0 mm. Texture: Smooth. Color: Mix of green (RHS 146D) and dark purplish-pink (RHS 186C); yellow-green (RHS 144C) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALGUAJO' differs from female parent plant '01-1859' (unpatented) in that 'PHALGUAJO' has oblong lateral lobes, rhombic apical lobes, and white, dotted whiskers, whereas '01-1859' has weakly spatulate lateral lobes, triangular apical lobes, and light purple whiskers. Additionally, 'PHALGUAJO' has smaller flowers than '01-1859'.

'PHALGUAJO' differs from male parent plant '22286-05' (unpatented) in that 'PHALGUAJO' has white, dotted columns and white, dotted whiskers, whereas '22286-05' has columns that are very light purple at the base and white toward the tip, and white whiskers.

'PHALGUAJO' is most similar to the commercial *Phalaenopsis* plants named 'PHALFAMZOL' (U.S. Plant Pat. No. 28,780) and 'PHALFYPCI' (U.S. Plant Pat. No. 26,961). 'PHALGUAJO' differs from the commercial variety 'PHALFAMZOL' in that 'PHALGUAJO' has white, dotted columns, whereas 'PHALFAMZOL' has white columns with a touch of lilac. Additionally, 'PHALGUAJO' has larger flowers and longer dorsal sepals than 'PHALFAMZOL'.

'PHALGUAJO' differs from the commercial variety 'PHALFYPCI' in that 'PHALGUAJO' has white, dotted columns, whereas 'PHALFYPCI' has purple columns. Additionally, 'PHALGUAJO' has larger flowers and longer dorsal sepals than 'PHALFYPCI'.

I claim:

1. A new and distinct variety of *Phalaenopsis* plant named 'PHALGUAJO', substantially as described and illustrated herein.

* * * * *